US 6,551,340 B1

(12) United States Patent
Kónya et al.

(10) Patent No.: US 6,551,340 B1
(45) Date of Patent: Apr. 22, 2003

(54) VASOOCCLUSION COIL DEVICE HAVING A CORE THEREIN

(75) Inventors: András Kónya, Houston, TX (US); Sidney Wallace, Houston, TX (US); Kenneth Carroll Wright, Houston, TX (US)

(73) Assignee: Board of Regents The University of Texas System, Austin, TX (US)

( * ) Notice: Subject to any disclaimer, the term of this patent is extended or adjusted under 35 U.S.C. 154(b) by 0 days.

(21) Appl. No.: 09/413,520

(22) Filed: Oct. 6, 1999

Related U.S. Application Data

(60) Provisional application No. 60/103,647, filed on Oct. 9, 1998.

(51) Int. Cl.[7] ............................................. A61M 29/00
(52) U.S. Cl. ............................................................. 606/191
(58) Field of Search ................................. 606/108, 195, 606/191, 198, 200

(56) References Cited

U.S. PATENT DOCUMENTS

| | | |
|---|---|---|
| 4,706,671 A | 11/1987 | Weinrib |
| 4,854,330 A | 8/1989 | Evans, III et al. |
| 4,917,102 A | 4/1990 | Miller et al. |
| 4,925,445 A | 5/1990 | Sakamoto et al. |

(List continued on next page.)

FOREIGN PATENT DOCUMENTS

| | | |
|---|---|---|
| DE | 3203410 | 11/1982 |
| DE | 19607451 | 2/1996 |
| DE | 29518932 | 8/1996 |
| EP | 0121447 | 2/1984 |
| EP | 0717969 | 12/1995 |

(List continued on next page.)

OTHER PUBLICATIONS

Cook Incorporated, "Detechable Embolization Coils", Bloomington, Indiana, 1996.
Cook Incorporated, "Embolization Microcoils", Bloomington, Indiana 1995.
Cook Incorporated, "Hilal Embolization Microcoils", Bloomington, Indiana 1988.
Craig, Andrew et al., "A New Percutaneous Vena Cava Filter". *AJR* 141, Sep. 1983.
U.S. application Ser. No. 09/139,494 filed Aug. 25, 1998, (Abstract and Drawings only).
U.S. application Ser. No. 08/923,061 filed Sep. 3, 1997, (Abstract and Drawings only).

*Primary Examiner*—Eduardo C. Robert
(74) *Attorney, Agent, or Firm*—Brinks, Hofer, Gilson & Lione

(57) ABSTRACT

A coil-type vasoocclusion device (10) for establishing an embolus or vascular occlusion in a human or veterinary patient is adapted for introduction into the patient via a catheter (32). The device (10) first includes a coil (12) having proximal and distal coil ends (16,18) and a coil lumen (20). The device (10) also includes a core (22) disposed in at least part of the coil lumen (20), the core having proximal and distal core ends (24,26). Only one core end (24 or 26) is directly affixed to a respective end (16 or 18) of the coil (12); the other core end (26 or 24) is not directly connected to either end (16 or 18) of the coil (12). The core (22) is preferably nitinol in a superelastic state, being in other than its stress induced, martensitic condition. The device (10) can include a thrombogenic material (38) connected to or carried by the coil (12). The coil (12) is preferably adapted to achieve a suitable secondary shape (60) when deployed from the catheter (32). A medical device (40) combining the catheter (32), a pusher (34), a coupling (30) and the vasoocclusion device (10) is also disclosed. The vasoocclusion device (10) is easily repositioned in the vascular system, thereby ensuring proper deployment, and also enjoys a dislodging force about twice as great as comparable coil-type devices lacking the core (22), substantially or completely preventing migration of the device (10) after its deployment.

31 Claims, 7 Drawing Sheets

U.S. PATENT DOCUMENTS

| | | | |
|---|---|---|---|
| 4,934,380 A | | 6/1990 | de Toledo |
| 4,935,068 A | | 6/1990 | Duerig |
| 4,994,069 A | * | 2/1991 | Ritchart et al. .............. 606/191 |
| 5,069,226 A | | 12/1991 | Yamauchi et al. |
| 5,108,407 A | | 4/1992 | Geremia et al. |
| 5,108,420 A | | 4/1992 | Marks |
| 5,122,136 A | | 6/1992 | Guglielmi et al. |
| 5,122,154 A | | 6/1992 | Rhodes |
| 5,133,709 A | | 7/1992 | Prince |
| 5,133,731 A | | 7/1992 | Butler et al. |
| 5,147,370 A | | 9/1992 | McNamara et al. |
| 5,167,624 A | | 12/1992 | Butler et al. |
| 5,171,383 A | | 12/1992 | Sagae et al. |
| 5,190,546 A | | 3/1993 | Jervis |
| 5,192,301 A | | 3/1993 | Kamiya et al. |
| 5,217,484 A | | 6/1993 | Marks |
| 5,226,911 A | | 7/1993 | Chee et al. |
| 5,234,003 A | | 8/1993 | Hall |
| 5,234,437 A | | 8/1993 | Sepetka |
| 5,242,759 A | | 9/1993 | Hall |
| 5,243,996 A | | 9/1993 | Hall |
| 5,250,071 A | * | 10/1993 | Palermo ..................... 606/198 |
| 5,261,916 A | | 11/1993 | Engelson |
| 5,267,955 A | | 12/1993 | Hanson |
| 5,304,194 A | | 4/1994 | Chee et al. |
| 5,365,943 A | | 11/1994 | Jansen |
| 5,411,476 A | | 5/1995 | Abrams et al. |
| 5,522,822 A | | 6/1996 | Phelps et al. |
| 5,540,680 A | | 7/1996 | Guglielmi et al. |
| 5,578,074 A | | 11/1996 | Mirigian |
| 5,582,619 A | | 12/1996 | Ken |
| 5,611,874 A | | 3/1997 | Zadno-Azizi et al. |
| 5,645,558 A | * | 7/1997 | Horton ...................... 606/191 |
| 5,649,949 A | | 7/1997 | Wallace et al. |
| 5,669,931 A | | 9/1997 | Kupiecki et al. |
| 5,700,258 A | | 12/1997 | Mirigian et al. |
| 5,720,300 A | | 2/1998 | Fagan et al. |
| 5,725,534 A | | 3/1998 | Rasmussen |
| 5,725,570 A | | 3/1998 | Heath |
| 5,749,891 A | | 5/1998 | Ken et al. |
| 5,797,857 A | | 8/1998 | Obitsu |
| 5,797,953 A | | 8/1998 | Tekulve |
| 5,957,948 A | | 9/1999 | Mariant |
| 6,001,068 A | | 12/1999 | Uchino et al. |

FOREIGN PATENT DOCUMENTS

| | | |
|---|---|---|
| EP | 0720838 | 12/1995 |
| EP | 0734697 | 3/1996 |
| EP | 0765636 | 4/1997 |
| EP | 0820726 | 7/1997 |
| SU | 1771719 | 10/1992 |
| SU | 1777842 | 11/1992 |
| WO | 9115152 | 10/1991 |
| WO | 9216163 | 10/1992 |
| WO | 9406502 | 3/1994 |
| WO | 9406503 | 3/1994 |
| WO | 9407560 | 4/1994 |
| WO | 9409705 | 5/1994 |
| WO | 9411051 | 5/1994 |
| WO | 9525480 | 9/1995 |
| WO | 9600104 | 1/1996 |
| WO | 9618343 | 6/1996 |
| WO | WO 97/42881 * | 11/1997 |

* cited by examiner

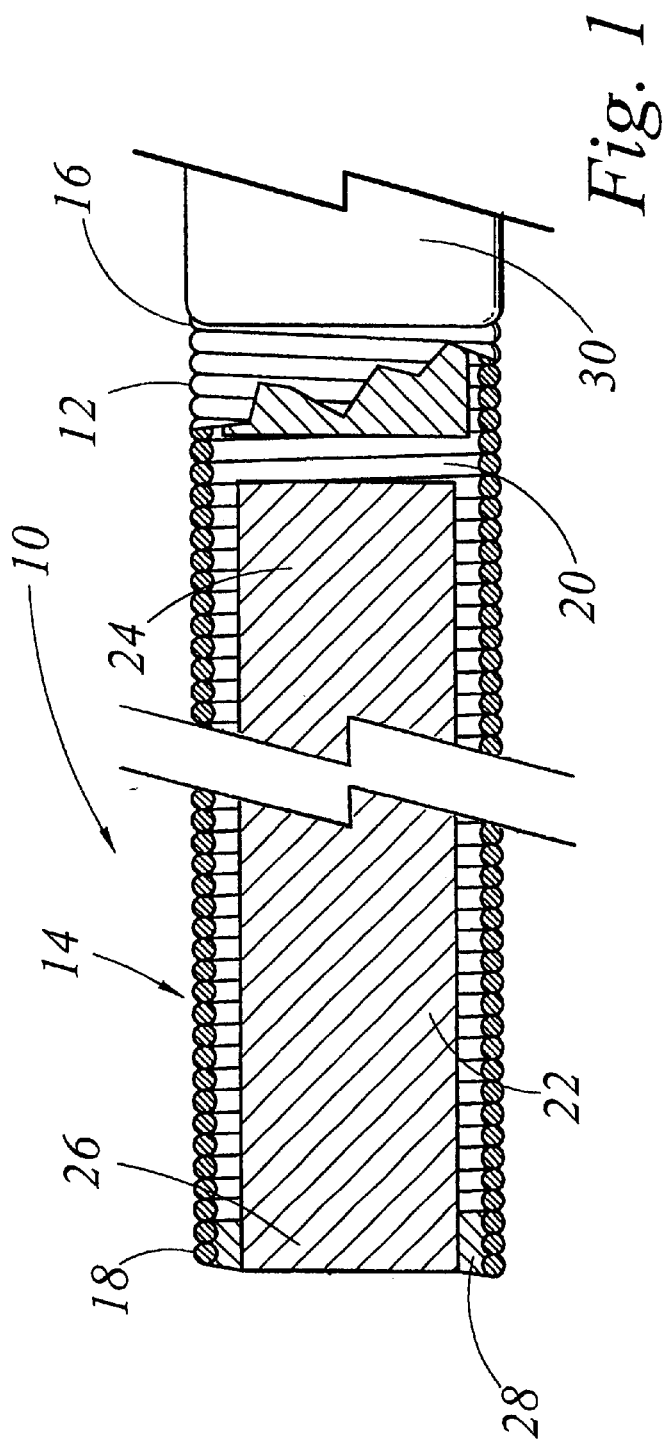
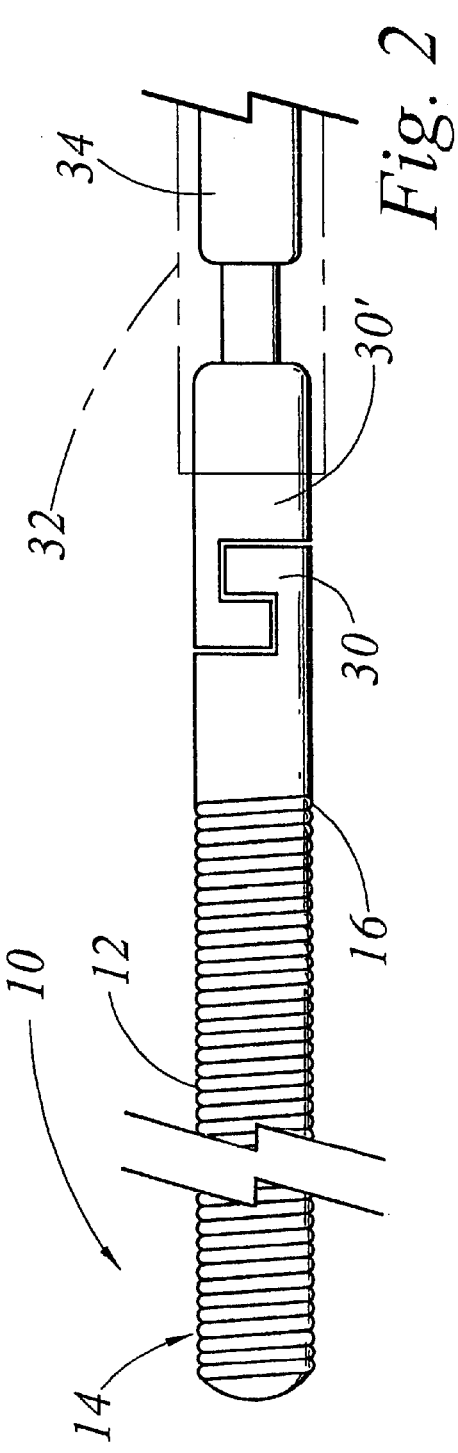

VASOOCCLUSION COIL DEVICE HAVING A CORE THEREIN

This application claims the benefit of No. 60/103,647 filed Oct. 9, 1998.

TECHNICAL FIELD

This invention relates generally to medical devices, and more particularly to embolization devices, that is, devices for occluding a portion of the vascular system of a human or veterinary patient.

BACKGROUND OF THE INVENTION

Embolization of vascular occlusion devices (hereinafter generally referred to as "vasoocclusion devices") are surgical implements or implants that are placed within the vascular system of a patient. Vasoocclusion devices are typically used either to block the flow of blood through a vessel by the formation of an embolus in the vessel, or to form such an embolus within an aneurysm stemming from the vessel. Such devices are conventionally introduced into the vascular system of the patient by a catheter, and can include a mechanical interlock to permit detachment of them from a pusher extending through the catheter.

A variety of prior implantable, coil-type vasoocclusion devices are known which include a coil having a lumen defined therein, and some kind of safety wire disposed in and extending through the lumen. The coils of such devices may themselves be formed into a secondary coil shape, or any of a variety of more complex secondary shapes adapted to the particular location at which an embolism or occlusion is to be established. A variety of thrombogenic materials may be attached to or carried by the coils of such devices to promote the formation of clots (thus, in turn, promoting the establishment of the embolism or occlusion), such as Dacron, polyester, silk or cotton fibers, filaments or the like. The coil itself, or the secondary coil shape, abuts or engages the wall of the vessel in which the device is disposed, serving to anchor the device in the vessel of interest.

For example, U.S. Pat. No. 4,994,069 to M. Ritchart et al., issued Feb. 19, 1991, discloses a flexible, coiled wire for use in small vessel occlusion. The wire has a stretched, linear condition in which it can be advanced through a catheter lumen to a selected vessel, and a relaxed, convoluted condition produced by a combination of helical windings of the wire and irregularities of the helical winding (referred to as a "memory"). The patent does not appear to suggest that the wire can itself be a conventional shape memory material, such as nitinol alloy.

Numerous similar devices have been disclosed. U.S. Pat. No. 5,749,891 issued May 12, 1998 and U.S. Pat. No. 5,582,619 to issued on Dec. 10, 1996, both to C. G. M. Ken et al., are directed to implantable vasoocclusion devices comprising a helically wound coil which is itself wound into a secondary shape. The devices can include an inner, stretch-resisting member positioned in the lumen of the coil. Possible materials for the wire making up either the coil or the inner member include stainless steel and nitinol. The device shown in FIG. 4 of the '891 patent can include multiple layers of coils, the inner member being a wire which prevents stretching of the coil during movement of it. The '619 patent also discloses a coil having a wire positioned therein to similarly prevent stretching.

U.S. Pat. No. 5,645,558 issued Jul. 8, 1997 to J. A. Horton, in FIG. 4 discloses a vasoocclusion device having a helical coil with a safety wire positioned therein for structural support. Alternatively, the internal wire may be preformed into an ultimately desired shape (for example, a sphere) and fed through the coiled strand, the coiled strand then assuming the shape of the safety wire.

Finally, FIG. 4 of U.S. Pat. No. 5,522,822 issued Jun. 4, 1996 to J. J. Phelps et al., discloses a vasoocclusion device which comprises a helical coil having an internal wire attached to end caps at both ends of the coil. The wire may be made of a shape memory material such as nitinol, while the coil is typically made of a radiopaque material such as tungsten, platinum, gold or silver.

The coil-type vasoocclusion devices in the last four of these patents can all be generally characterized in that the proximal and distal ends of the safety wire are affixed or directly secured to the respective proximal and distal ends of the coil itself. Each of these devices is of course subject to its own advantages and drawbacks during use. In general, however, and without ascribing this drawback to any of the devices disclosed in these particular patents, commercially available vasoocclusion coils do not anchor well in the target vessel and/or do not attain a shape which effectively occludes blood flow when deposited in the target vessel. This is because the only thing by which such commercially available coils apply an anchoring force against the wall of the target vessel, is the abutment force provided by the resilient return of the coils themselves to a desired shape.

It would be highly advantageous to have a coil-type vasoocclusion device in which the assistive force provided by the core to anchor the device at the location of interest, could be adjusted or selected to provide an optimal total anchoring force for the device. It would also be highly advantageous to have a coil-type vasoocclusion device which maximizes the assistive force provided by the core to anchor the device at the location of interest. It would further be highly advantageous to have a coil-type vasoocclusion device which could more readily be removed or repositioned than could prior coil-type vasoocclusion devices.

SUMMARY OF THE INVENTION

The foregoing problems are solved and a technical advance is achieved in an illustrative vasoocclusion device. More particularly, the device of the present invention is directed to a rapidly and reliably deployable and repositionable, self-anchoring, mechanical vascular occluder whose shape and anchoring force are predetermined by an included core having a shape memory. The device of the present invention is a coil-type vasoocclusion device having a coil with a coil lumen defined therein, the core being disposed in part or more of the coil lumen. The core can be composed of a nitinol or other shape memory material, preferably in a superelastic state, or can be composed of stainless steel, MP35N or the like. (If nitinol material is used, the nitinol need not be in its stress induced, martensite condition, however, and preferably is not in such a condition.) The core is "springy" and provides an additional, anchoring assistive force, which supplements the anchoring force provided by the coil itself and which can improve the effectiveness of the coil in several applications. The present invention can be further characterized in that, unlike comparable coil-type devices, the nitinol or other shape memory material core is not affixed to the coil at both of its ends. Instead, only one portion of the core is affixed to the coil, preferably one end of the core being affixed at or near one end of the coil, while the remainder of the core is not affixed to the coil.

Such an arrangement of fixing the core to the coil may advantageously allow an adjustment of the assistive anchoring force provided by the core to a coil of a given length, by selection of the length of the core. Such an arrangement may also maximize the assistive anchoring force provided by the core, since such force would not be diminished by any twisting of the core during manipulation or positioning of the coil. Further, such an arrangement may facilitate removal or repositioning of the device, since elongation of the coil when subjected to a longitudinal removing force may lessen the anchoring force supplied by the coil itself, making engagement with the introducing or removal apparatus easier.

In a first aspect, then, the present invention is directed to a vasoocclusion device for establishing an embolus or vascular occlusion in a human or veterinary patient, the device comprising: a coil having a proximal coil end, a distal coil end spaced from the proximal coil end and a coil lumen defined therein extending between the proximal coil end and the distal coil end; and a core disposed in at least part of the coil lumen, the core having a proximal core end and a distal core end; and wherein one portion of the core is affixed to the coil at a selected location, whereby the core provides the coil with an anchoring force in a vessel of the human or veterinary patient.

Preferably, the coil lumen possesses a defined cross-section, and the core can but need not substantially fill the defined cross-section of the coil lumen. Also preferably, the distal core end is directly affixed to the distal coil end in any convenient manner, for example, by solder, welding or adhesive.

The diameter of the core is selected so as to provide a desired assist to the expansile or anchoring force of the coil. Such force can be adjusted over a relatively wide range. The core can extend through the entire lumen of the coil, or can instead extend in only part of the lumen, for example, from either the proximal or distal end of the coil. This leaves the remaining part of the coil highly flexible, or "floppy."

In certain embodiments, the core has a changing diameter. In one, the core tapers toward its free end, that is, an end which is not affixed to the respective coil end; by using a tapered nitinol wire, the assistive forces of the coil can be even more precisely adjusted along the coil. In another, both end-portions of the core are tapered; as a result, the coil's expansive force will be the greatest at its mid-portion, while the coil strength will be evenly reduced toward the ends. Consequently, it is the mid-portion of the coil that will mostly anchor the device within the vasculature while the moderately reinforced end-portions allow for better coverage of the center space of the vessel resulting in quicker occlusion.

In a further embodiment, the core is formed from a nitinol wire whose diameter alternates between a larger and a smaller caliber, and the transition between the larger and smaller caliber segments is even and continuous without step formation. This technical solution makes it possible to use relatively great assistive forces to anchor the device, but simultaneously preserves the pliability or flexibility of the coil to a certain degree, facilitating both the proper arrangement of coil turns within the vasculature and pushability of the coil through the delivery catheter.

The vasoocclusion device is preferably adapted for introduction into the patient via a catheter, the device being detachably secured to the catheter. More particularly, the device is preferably adapted for introduction via a pusher contained in the catheter, and the device further comprises a reversible coupling for detachably connecting the device to the pusher.

As indicated, the core preferably comprises nitinol, another shape memory material, stainless steel or MP35N. The nitinol is preferably in a superelastic state, but is in a condition other than its stress induced, martensitic condition.

The coil of the vasoocclusion device can comprise any convenient non-linear secondary shape upon its deployment in the patient. The secondary shape can be a saddle-type, helical type, vortex-type, irregular baffle-type, fusiform helix-type or oval plate shape. It may also be spherical, derived from circular or D-shaped or semicircular shapes of the helical turns. The vasoocclusion device preferably further comprises a thrombogenic material connected to or carried by the coil, such as Dacron, silk, cotton, wool or polyester threads.

In a second aspect, the present invention is directed to a specific combination of the features mentioned above. More particularly, it is directed to a vasoocclusion device for establishing an embolus or vascular occlusion in a human or veterinary patient, the device being adapted for introduction into the patient via a catheter, and the catheter having a pusher contained therein for deploying the device from the catheter; the device comprising: a coil having a proximal coil end, a distal coil end spaced from the proximal coil end and a coil lumen defined therein extending between the proximal coil end and the distal coil end; a core disposed in at least part of the coil lumen, the core having a proximal core end and a distal core end; and a thrombogenic material connected to or carried by the coil; wherein the distal core end is affixed to the distal coil end by solder, welding, or an adhesive; wherein the core comprises nitinol in a superelastic state, being in other than its stress induced, martensitic condition; wherein the thrombogenic material comprises Dacron, cotton or polyester threads; wherein the coil (12) comprises a wire (14) having a diameter of about 0.010 in. to about 0.032 in. (about 0.25 mm to about 0.81 mm); wherein the core (22) has a diameter of about 0.004 in. to about 0.015 in. (about 0.10 mm to about 0.38 mm); wherein the coil (12) is about 2 to about 40 cm long when constrained within a catheter; and wherein the core provides the coil with an additional force assisting anchoring of the coil in the human or veterinary patient when the coil and the core are deployed from the catheter.

In a third aspect, the present invention is directed to the combination of the coil and core device with the catheter and pusher for deploying the device in the patient. Thus, in its third aspect, the present invention is directed to a medical device for establishing an embolus or vascular occlusion in a human or veterinary patient, comprising: a coil having a proximal coil end, a distal coil end spaced from the proximal coil end and a coil lumen defined therein extending between the proximal coil end and the distal coil end; and a core disposed in at least part of the coil lumen, the core having a proximal core end and distal core end; wherein one portion of the core is affixed to the coil at a selected location; a catheter dimensioned to receive the coil and the core therein; and a pusher contained in the catheter, adapted to deploy the coil and the core from the catheter; wherein the core provides the coil with an additional force assisting anchoring of the coil in the human or veterinary patient when the coil and the core are deployed from the catheter. This third aspect of the present invention preferably further comprises a coupling for detachably connecting the coil to the pusher.

In a fourth and final aspect, the present invention is directed to an improvement in a coil-type vasoocclusion device for establishing an embolus or vascular occlusion in a vessel of a human or veterinary patient, the device comprising: (a) a coil having a proximal coil end, a distal coil end spaced from the proximal coil end, a coil lumen defined therein extending between the proximal coil end and the distal coil end; and (b) a core disposed in at least part of the coil lumen, the core having a proximal core end and a distal core end; the improvement being characterized in that one and only one of the proximal core end and the distal core end is affixed to the coil proximate to a respective one of the proximal coil end and the distal coil end, the other of the distal core end and the proximal core end not being affixed to either the distal coil end or the proximal coil end; and wherein the core provides the coil with an anchoring force in the vessel.

As indicated above, the vasoocclusion device of the present invention may possess significant advantages over prior coil-type vasoocclusion devices. It may be possible to adjust the assistive anchoring force provided by the core to a coil of a given length, by selection of the length of the core. Since one end of the core is free and not affixed to an end of the coil, the assistive anchoring force provided by the coil may be maximized, and not diminished by any twisting of the core during manipulation or positioning of the coil. Finally, such an arrangement may facilitate removal or repositioning of the device, since elongation of the coil when subjected to a longitudinal removing force may lessen the anchoring force supplied by the coil itself, making engagement with the introducing or removal apparatus easier. Of course, in contrast to comparable stainless steel coils lacking the nitinol or other core, the vasoocclusion device possesses significantly enhanced self-anchoring capability, which is expected to result in the substantial reduction or elimination of migration of the installed coil. Further, however, the vasoocclusion device is rapidly and readily repositionable after deployment in a patient. Advantageously, the vasoocclusion device can often be deployed into a patient through the same catheter as is used for comparably-sized stainless steel coils.

BRIEF DESCRIPTION OF THE DRAWING

A better understanding of the present invention will now be had upon reference to the following detailed-description, when read in conjunction with the accompanying drawing, wherein like reference characters refer to like parts throughout the several views, and in which:

FIG. 1 is a partial longitudinal section view of a first embodiment vasoocclusion device of the present invention;

FIG. 2 is a side view of the device of FIG. 1;

DETAILED DESCRIPTION

Figure 3:
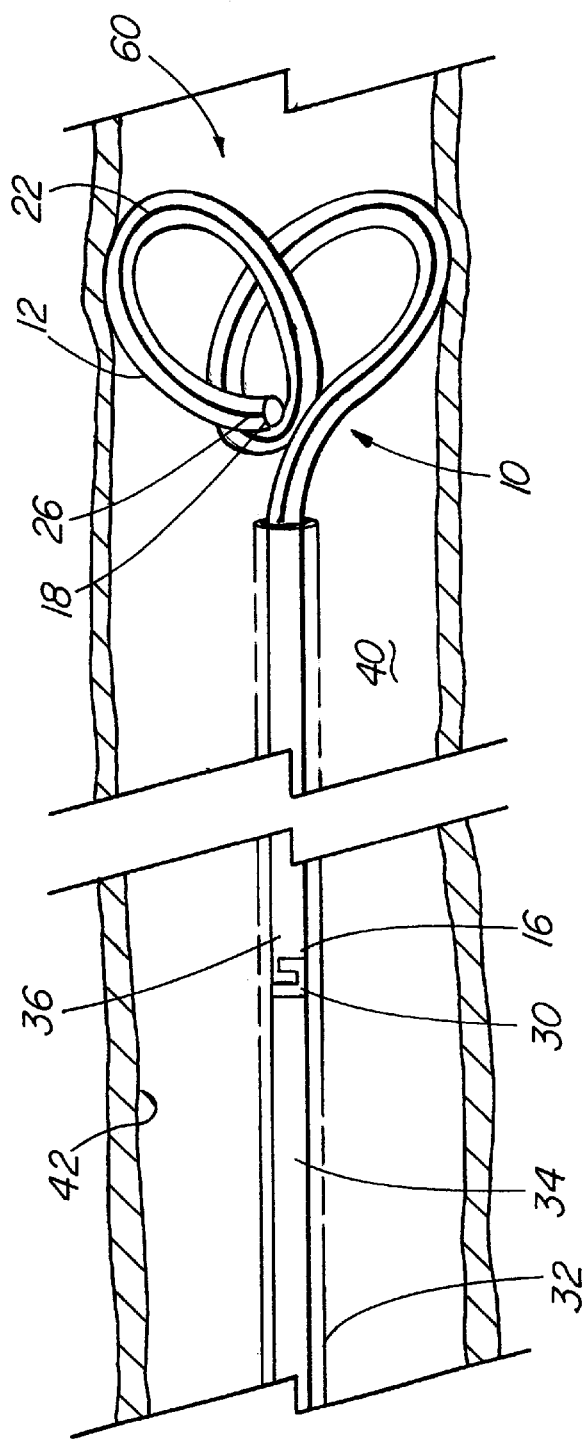
FIG. 3 is a partial cross-sectional view of the device of FIGS. 1 and 2.

With reference first to FIGS. 1 and 2, a first embodiment of a coil-type vasoocclusion device 10 as set forth in the present invention is thereshown, useful for establishing an embolus or vascular occlusion in a human or veterinary patient. The vasoocclusion device 10 of the present invention first comprises a coil 12 composed of a wire 14 of stainless steel or another suitable medical grade material. The individual loops of wire 14 preferably lie closely together in forming the coil 12. The coil 12 has a proximal coil end 16 and a distal coil end 18 spaced from the proximal coil end 16. The coil 12 also has a coil lumen 20 defined therein, extending between the proximal coil end 16 and the distal coil end 18. This is, of course, the simplest conformation of the coil 12; more complex shapes for the coil 12 itself can be employed as appears appropriate for the particular use to which the device 10 is to be put.

The vasoocclusion device 10 next comprises a core 22 disposed in at least part of the coil lumen 20. The core 22 need not extend the entire length of the coil lumen 20. To the contrary, it may facilitate some uses of the device 10 to allow part of the coil 12 to remain "floppy," that is, unsupported by the core 22. The core has a proximal core end 24 and a distal core end 26 spaced from the proximal core end 24. Preferably, the distal core end 26 is located adjacent to the distal coil end 18. It is a characterizing feature of the invention, however, that unlike the prior art devices mentioned above, the core 22 is affixed to the coil at one selected location, such as one and only one of the proximal and distal coil ends 24,26 is affixable or affixed to or near a respective one of the proximal and distal coil ends 16,18 and in particular, distal core end 26 to the distal coil end 18, as seen in FIG. 1. The other of the distal and proximal core ends 26,24 is not affixable or affixed to an end 16,18 of the coil 12. The distal core end 26 can be affixed to the distal coil end 18 by a drop solder, or by welding, or by a suitable adhesive or the like.

With particular reference now to FIG. 3, the vasoocclusion device 10 is preferably adapted for introduction into, for example, a vessel 42 of the human or veterinary patient via a catheter 32, as a medical device assembly 40. The specific nature of the catheter 32 itself is pertinent to the use of the device 10 only insofar as the material of the catheter 32 must be selected to allow the free movement of the coil 12 within the catheter 32. Otherwise, any of a variety of catheter configurations are expected to be useful for the catheter 32, such as the well known "hockey stick" style catheter. For example, when the coil 12 includes a thrombogenic material in the manner described below, the catheter 32 should be made of a material which does not develop frictional binding with the thrombogenic material. A catheter 32 composed of polytetrafluoroethylene (PTFE), for example, may be necessary when some thrombogenic materials are used on the coil 12.

In any event, the vasoocclusion device 10 is preferably secured to the catheter 32 in a detachable manner. More preferably, the device 10 comprises a reversible coupling 30 for detachably connecting the device 10 to the catheter 32 for introducing the device 10 into the patient. Even more preferably, the device 10 is further adapted for introduction into the patient via a pusher wire or pusher 34 contained within the catheter 32. The coupling 30 then detachably connects the device 10 to a complementary coupling 30' of the pusher 34. A variety of couplings for this purpose are known, and the selection of any particular one should be made in dependence upon the construction of the catheter 32, the coil 12 and the target location for deployment of the device 10. The coupling 30,30' shown in FIG. 2 is a conventional interdigitating connection.

Deployment of the device 10 from the catheter 32 is remarkably straightforward. The device 10 is engaged with the pusher 34 via the coupling 30 and withdrawn into the catheter 32 in a straight condition. The catheter 32 is then introduced into the patient and advanced until its distal end is adjacent the target location for deployment of the device 10. The pusher 34 is then advanced to deploy the device 10, and the coupling 30 actuated to detach the device 10 from the pusher 34. Retrieval of the device 10, for either removal from the patient or repositioning in the patient, is carried out by reversing these steps.

Figure 4:
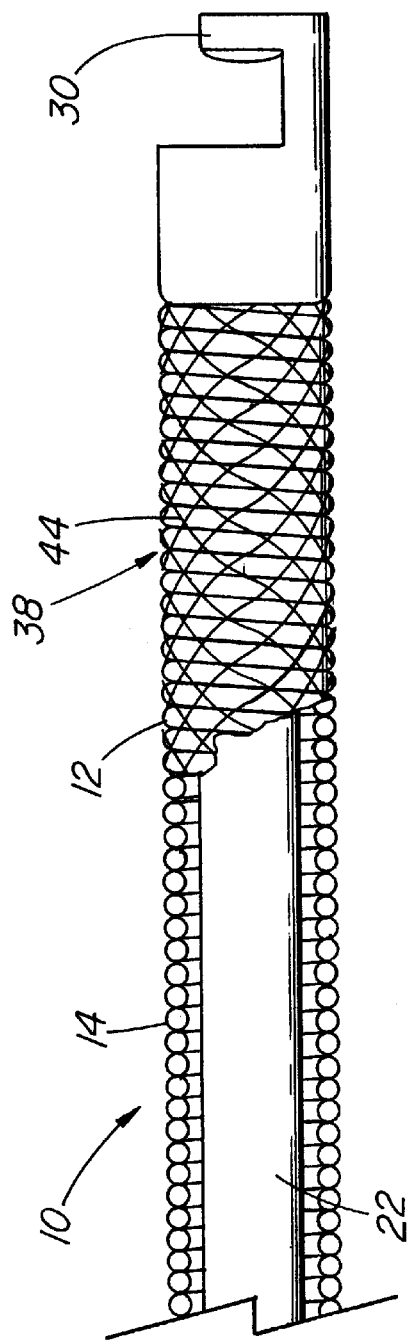
FIG. 4 is a partially sectioned side view of another embodiment of vasoocclusion device of the present invention showing thrombogenic material.

As indicated above, it is preferred for some uses of the device 10 that a thrombogenic material 38 (FIG. 4) be connected to or carried by the coil 12. The thrombogenic material 38 can be any material conventionally used for this purpose, for example, Dacron, silk, cotton, wool or polyester. Other suitable materials are of course known. The thrombogenic material 38 can be configured as threads, either looped or meshed, or braided as in FIG. 4. Those skilled in the art will be well aware of other configurations for the thrombogenic material. In FIG. 4, a braided fibrous mesh 44 of threads of thrombogenic material 38 extends around and along coil 12.

The core 22 provides the coil 12 with an additional force which assists anchoring of the coil 12 in the human or veterinary patient. The amount of such additional force is selected by choosing the composition, diameter and length of the core 22. For example, the core 22 can substantially fill the cross-sectional area of the coil lumen 20, if desired. However, the device 10 can work quite well with a core 22 of smaller diameter.

The core 22 can be composed of any of several materials which provide an additional force to assist the anchoring of the coil 12. Preferably, however, the core 22 comprises nitinol, another shape memory material, stainless steel or MP35N superalloy (SPS Corporation, Jenkintown, Pa.). More preferably, the core 22 comprises nitinol in its superelastic state. However, it is also preferred that the nitinol not be in its stress induced, martensitic condition.

In other embodiments, the core 22 has a changing diameter. In a preferred embodiment, seen in FIG. 5, it tapers toward its free end, that is, which is not affixed to the respective coil end, defining a tapered end portion 46. By using a tapered nitinol wire, the assistive forces of the core can be even more precisely adjusted along the coil. In another embodiment (FIG. 6), both end-portions 46 of the core 22 are tapered. As a result, the coil's expansive force will be the greatest at its cylindrical mid-portion, while the coil strength will be evenly reduced toward the ends. Consequently, it is the mid-portion of the core 22 that will mostly anchor the device within the vasculature while the moderately reinforced end-portions allow for better coverage of the center space of the vessel resulting in quicker occlusion.

Figures 5, 6, 7:
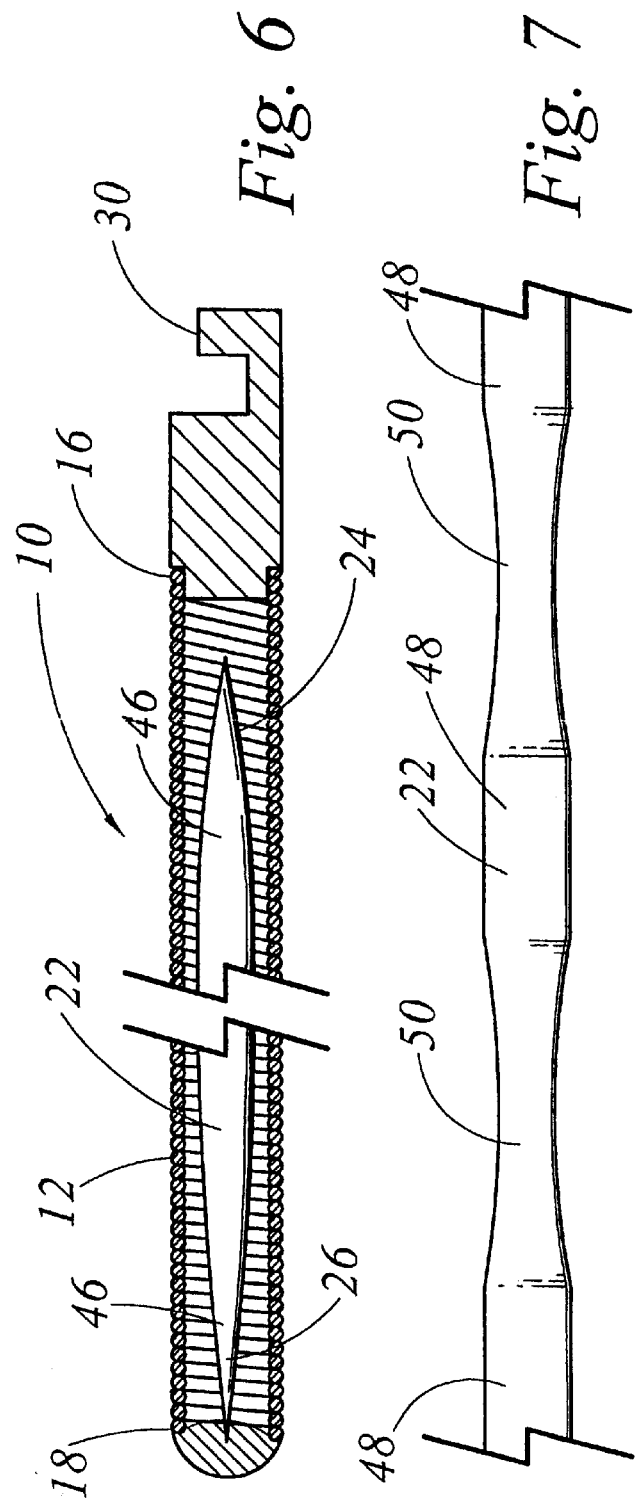
FIGS. 5 and 6 are partial longitudinal cross-section views of the device showing other embodiments of cores.
FIG. 7 is an elevation view of another embodiment of core of the present invention.
Figure 10:
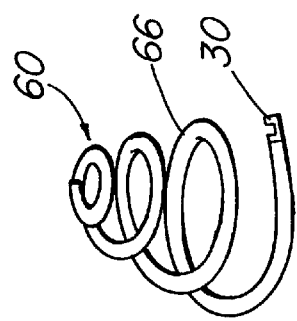
FIGS. 10 through 13 are isometric views of other embodiments of secondary shapes of vasoocclusion devices of the present invention.
Figure 13:
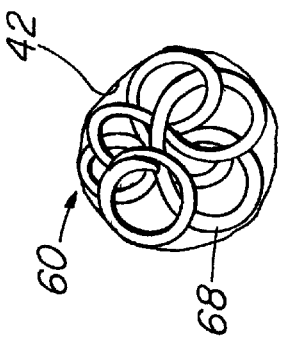
Figure 9:
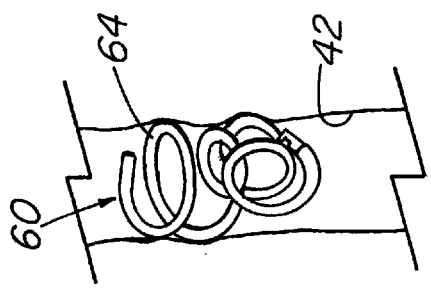
FIG. 9 is a partial cross-sectional view, similar to FIG. 8, of another embodiment of secondary coil shape.

It can be seen, with reference to FIGS. 5 and 6, that either distal end 26 of core 22 or distal coil end 18 for example can include means (such as an amount of adhesive) for affixing the distal core end to the distal coil end, so that the device can be shipped prior to assembly of the core within the coil lumen. Distal coil end 18 is rounded, as can be seen. Also, a detachable interlocking clip (not shown) may be utilized to affix a portion of the core to the coil.

FIG. 7 illustrates a further embodiment, wherein the core 22 is formed from a nitinol wire whose diameter alternates between a larger and a smaller caliber. The transition between the larger 48 and smaller 50 caliber segments is even and continuous without step formation. This technical solution makes it possible to use relatively great assistive forces to anchor the device, but simultaneously, by weakening the core at several sites, the pliability/flexibility of the coil can be preserved to a certain degree. This will facilitate both the proper arrangement of coil turns within the vasculature and pushability of the coil through the delivery catheter.

Figure 12:
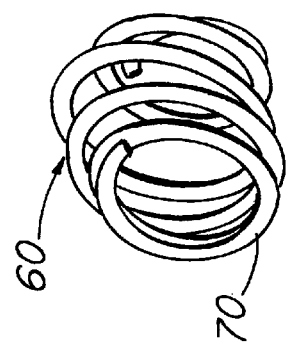
Figure 8:
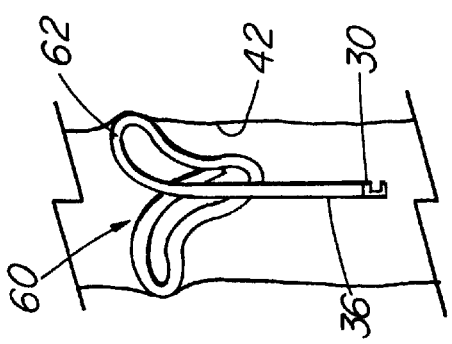
FIG. 8 is a partial cross-sectional view of the device of FIGS. 1 to 3 during use depicting a secondary coil shape.
Figure 11:
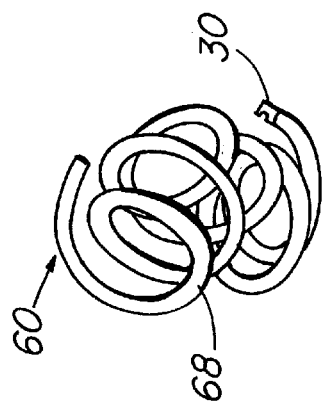

With reference now to FIGS. 8 through 13, it is preferred that the coil comprise a non-linear secondary shape 60 when deployed in the patient, for example, in a vessel 42 (see FIG. 13) The non-linear secondary shape 60 is supported by the core 22 (FIG. 3) and serves as an anchor for keeping the device 10 in position in the vessel 42, that is, for preventing unintended migration of the device 10 once it has been deployed in the vessel 42. A variety of secondary shapes for anchoring other coil-type devices are well known. The secondary shape 60 of the device 10 may comprise a saddle-type shape 62 (FIG. 8), a helical-type shape 64 (FIG. 9), a vortex-type shape 66 (FIG. 10), an irregular baffle-type shape 68 (FIGS. 11 and 13) or a fusiform helix-type shape 70 (FIG. 12).

With reference again to FIG. 3, one caveat should be noted with regard to the secondary shape 60, associated with the recovery or recapture of the device 10 by the catheter 32, and in particular, with engagement of the pusher 34 with the coupling 30 on the device 10. Recovery or recapture may be facilitated if the proximal or tail portion 36 of the coil 12 (extending distally from the proximal coil end 16) is kept straight, without any curve in it. This is particularly important if the proximal coil end 16 contains the proximal end 26 of the core, and even more important if the proximal core end 26 is affixed to the proximal coil end 16. Ideally, however, a short portion of the coil adjacent to the proximal coil end 16 is made without core reinforcement. Maintaining a straight proximal coil end portion 36 is also important for allowing the coil 12 to be readily pushed within the catheter 32 by the pusher 34, particularly when a relatively large diameter core 22 is employed. A non-reinforced coil (like a traditional spring coil) even with a curve usually does not interfere with the pushability of the coil through the delivery catheter.

Figure 14:
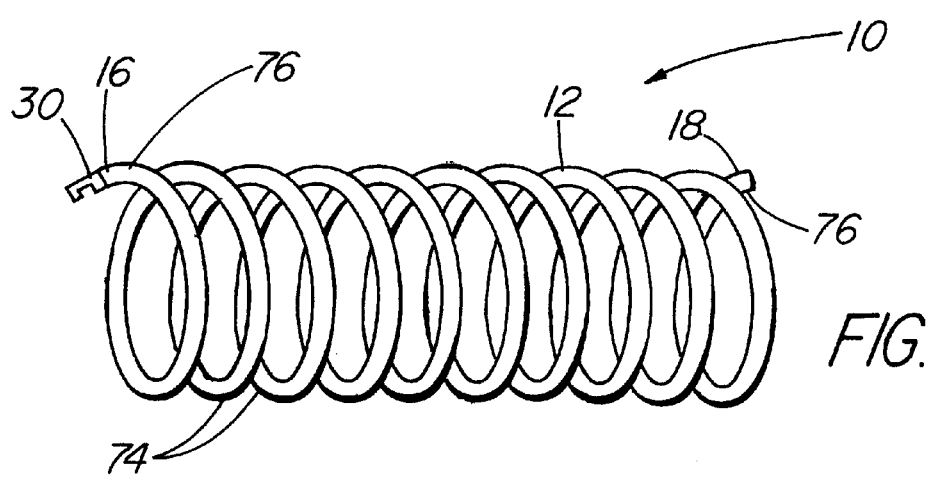
FIGS. 14 to 19 are additional embodiments of the device of the present invention associated with a spherical secondary coil shapes as seen in FIGS. 18 and 19 formed from circular (FIG. 15) or D-shaped (FIG. 16) helical coil turns.
Figure 17:
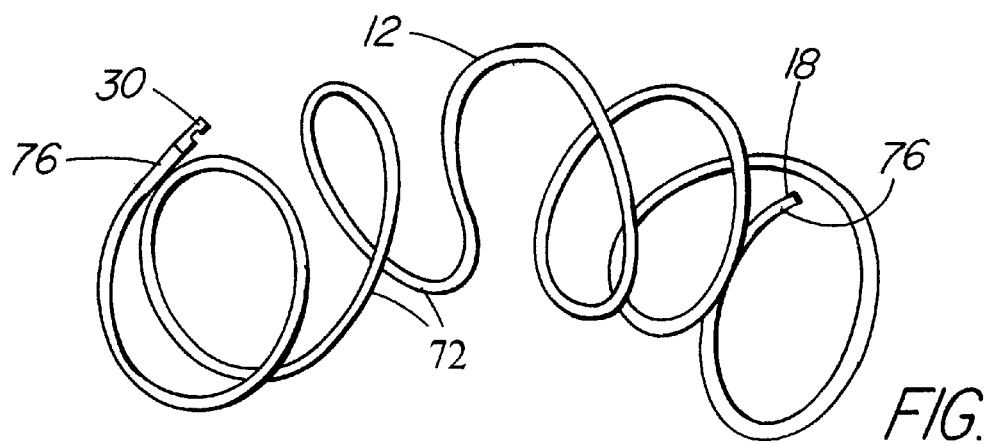
Figure 18:
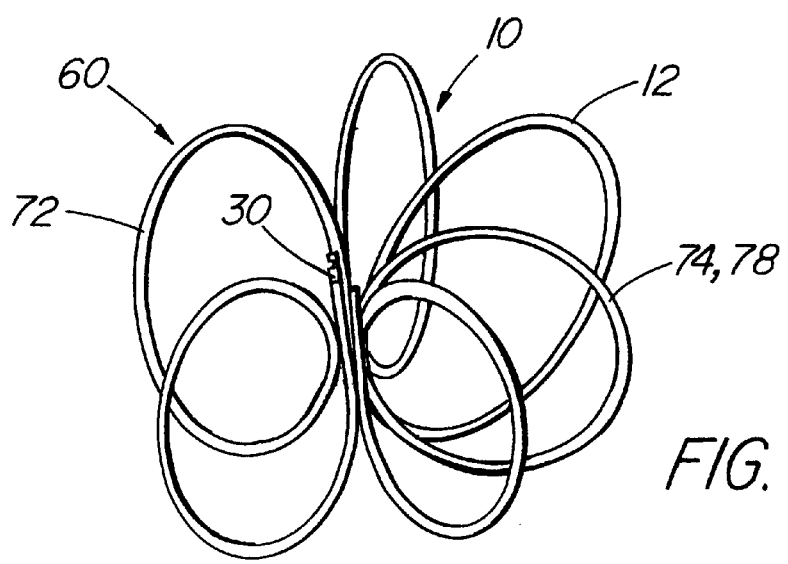
Figure 15:
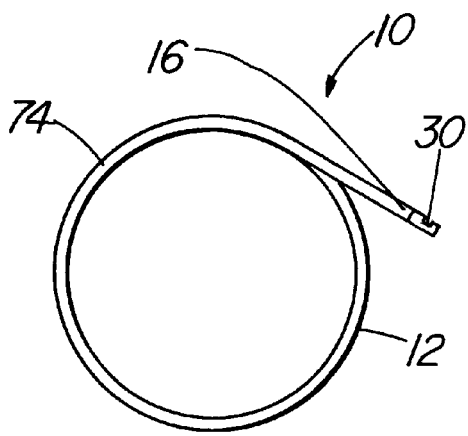
Figure 19:
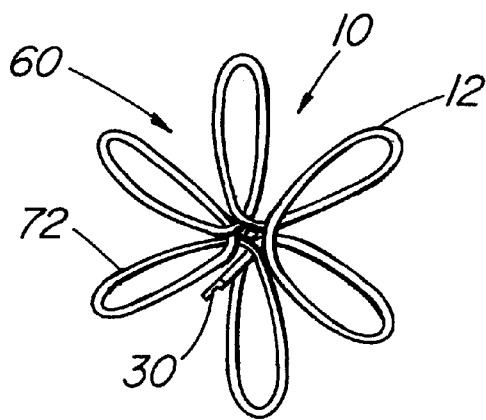

In a further possible embodiment and with reference now to FIGS. 14 to 19, a complex, substantially spherical secondary shape 72 is created from a series of helical turns (FIG. 14) spaced angularly about an axis. The shape of these turns may be, for example, circular (round) 74 as in FIG. 15, or D-shaped 78 as in FIG. 16. FIG. 14 shows a series of helical turns 74 initially aligned longitudinally. To make the complex, substantially spherical secondary shape 72, the two end-turns 76 of the helix should be held and then approached to each other to first form a semicircle from the helix (FIG. 17). By continuing to approach the end-turns 76 to one another until the circle is completed, a complex, substantially spherical secondary shape 72 is created (FIG. 18 and FIG. 19). By doing so, the central portion of each turn forms a vertical segment in the center of the device. This vertical segment is more prominent (and actually vertical) if the turns are D-shaped 78 as in FIG. 16. The central, vertical portions 80 of the D-shaped turns 78 can move beside and/or toward each other if the outer convex portions 82 of the D-shaped turns 78 are pressed together from outward. This is the case, when the above-described complex spherical secondary shape 72 is deployed in a vessel. Depending upon the relationship between the diameters of the occluder and the vessel, the complex coil will be constrained to a certain degree by the vessel wall, similar to the arrangement shown in FIG. 3. As a result, the regular shape of the design will be distorted to a certain extent, and simultaneously the device will be effectively anchored.

Figure 16:
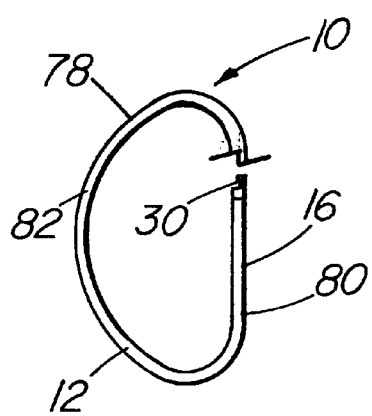

The features of the substantially spherical secondary shape 72 depicted in FIGS. 14 to 19 which are advantageous in particular are:

a) the described arrangement of the coil can produce a better coverage of the vascular space resulting in a quicker occlusion;

b) the self-anchoring capability of the occluder will be ideal, as the coil will press against the vessel wall at several points;

c) being substantially spherically shaped, the occluder does not require any particular orientation within the vasculature to achieve the best possible occlusion effect, so the occlusive capacity of the design is very similar whatever its orientation within the given space; and d) because of its spherical shape, the given cross-section of the vessel to be occluded will be evenly covered resulting in fast occlusion and minimal chance for recanalization; (the traditional helical coils are basically aligned along the circumference of the vessel leaving the center of the vessel unoccupied;) the ideal spherical shape can be approached better if the coil turns are formed with a D-shape as seen in FIG. 16.

Figure 20:
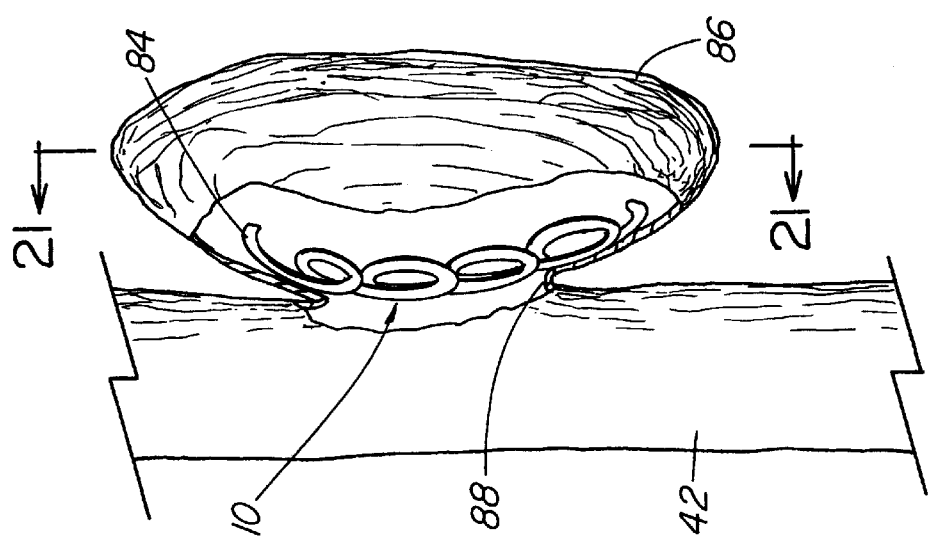
FIG. 20 is a partial cross-sectional view of another embodiment of the present invention during use in treating an aneurysm.
Figure 21:
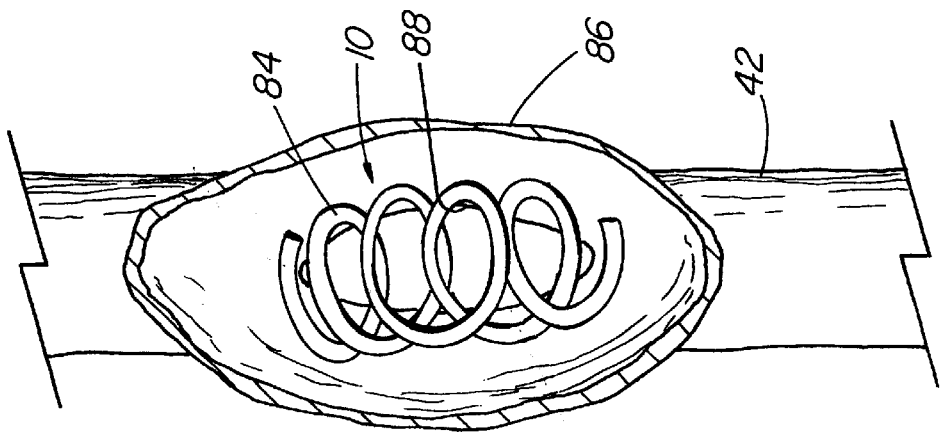
FIG. 21 is a partial cross-sectional view taken along line 21—21 of FIG. 20.

An additional embodiment of a secondary shape for device 10 is illustrated in FIGS. 20 and 21 especially suitable for treatment of wide neck aneurysms. FIG. 20 (lateral) and FIG. 21 (antero-posterior view) depict a wide neck aneurysm 86 in a vessel 42. The wide aneurysm neck 88 poses a significant problem to embolotherapy, since it is not able to prevent protrusion of coil turns deployed within the sac of the aneurysm. Apprehensive of causing inadvertent thrombosis in the parent vessel, the interventional radiologist often has to leave the neck unoccupied by the coil. The incomplete occlusion may result in further expansion and, possibly, consequent rupture and/or recurrence of the aneurysm.

In the protective embodiment of device 10 of the present invention shown in FIGS. 20 and 21, a series of helical turns of the reinforced coil of device 10 are arranged in a generally flattened array so that they can form a virtual flat, oval plate 84 (like a platter), with a general size greater than the aneurysm neck. Even more preferably, the oval plate 84 is bent circumferentially providing the plate with some depth and making it concave (seen from inside) or convex (seen from outside). The reinforced coil is preferably deployed within the aneurysmal sac around the rim or periphery of the aneurysmal neck 88 with its convexity facing the parent vessel 42. As a result, the coil abuts the aneurysm wall adjacent to the neck 88 at several points about its periphery ensuring good fixation of the device. In this special protective embodiment and the associated method, this type of coil is used to cover the wide neck 88 forming a relatively loose mesh. Through the plurality of holes of this mesh other, additional coils will then subsequently be deployed to fill the aneurysmal sac as much as possible; consequently, this type of coil is preferably not provided with any type of thrombogenic material. The goal of the protective coil having the special "oval plate" secondary shape 84 is to prevent coil protrusion and to promote complete embolization of the aneurysmal sac.

The specific dimensions of the coil 12 and core 22 of FIGS. 1 to 21 should be selected in light of the particular occlusive function to be performed by the device 10 at the target location in the patient. By way of example, the coil 12 can typically have an overall length of about 2 cm to about 40 cm, such a length being when constrained in an elongated shape within the catheter, or being considered before the establishment of any secondary shape 60 for the coil 12. Each loop of wire 14 of coil 12 can typically have an outside diameter of about 0.010 in. to about 0.032 in. (about 0.25 mm to about 0.81 mm), while the core 22 can typically have a diameter of about 0.004 in. to about 0.015 in. (about 0.10 mm to about 0.38 mm). The loops of wire 14 may be manufactured by utilizing fine wire having a diameter of 0.003 in. to about 0.005 in. (about 0.076 mm to about 0.126 mm). The secondary shape 60 of coil 12 may have a diameter of about 3 mm to about 15 mm. Where a nitinol core is used having a diameter of about 0.004 in. to about 0.006 in. (about 0.10 mm to about 0.15 mm), the coil may have a diameter of about 0.010 in. to about 0.015 in. (0.25 mm to 0.38 mm). These dimensions are, of course, merely examples. The specific dimensions of any particular embodiment of the vasoocclusion device 10 will depend upon the particular occlusion to be established.

As indicated previously, the present invention is also directed to a medical device 40 (see FIG. 3) for establishing an embolus or vascular occlusion in a human or veterinary patient. The medical device 40 comprises the coil 12, the core 22, the catheter 32 and the pusher 34 described above, and preferably also includes the coupling 30 described above.

The vasoocclusion device 10 of the present invention is expected to find utility in the performance of a wide range of procedures. For example, the improved anchoring enjoyed by the device 10 may allow it to be used in non-tapering territories of the vascular system. It is believed that coil-type devices have not previously been used in non-tapering territories because of the high likelihood of migration of the coil-type devices. The device 10 of the present invention may also find use in treating arteriovenous malformations and fistulas, in lesions of both the extremities and the lungs.

Another possible use of the device 10 of the present invention might be the occlusion of patent ductus arteriosus (PDA). Failure of prior devices to achieve successful closure of PDAs (especially those of larger diameter) is relatively frequent, because the interventional radiologist seeks to avoid complete occlusion through fear of causing inadvertent coil embolization. The device 10 may be useful with larger diameter lesions than has been possible with prior coils, while simultaneously improving safety of this type of vessel occlusion, due to the greater self-anchoring it enjoys. Except for very short lesions, the device 10 should have an advantage over several prior vascular occluders in that the device 10 is considerably smaller than those occluders and requires a smaller sized delivery system.

Yet another potential use of the device 10 is the safe exclusion of chronic pseudoaneurysms from the circulatory system. The device 10 might be easier to use than conventional coil(s) in combination with the spider-type devices presently employed for that purpose, avoiding known complications associated with such devices.

Vasoocclusion device 10 may also achieve a significant role in the non-surgical management of patients with systemic-to-pulmonary collateral vessels and shunts; in the embolization treatment of coronary artery fistulas; and in embolization treatments on the venous side, for example, in the treatment of varicoceles or aberrant vessels.

The vasoocclusion device 10 of the present invention possesses significantly enhanced self-anchoring capability over that of comparable stainless steel coils lacking the disclosed nitinol core. Dislodgment force tests carried out on devices deployed into the branches of the superior mesenteric artery (SMA) in pigs, disposed in the abdominal aorta and the inferior vena cava of pigs or positioned within a plastic tube indicate that the device 10 requires a dislodgment force of about twice the force required to dislodge comparable stainless steel coils lacking the disclosed core.

It should be clear that the present invention provides a coil-type vasoocclusion device 10 which may possess significant advantages over prior devices for that purpose. It may be possible to adjust the assistive anchoring force provided by the core of the device to a coil of a given length, by selection of the length of the core. Changing the diameter of the core is another way to find the optimal anchoring forces of the device. Since one end of the core is free and not affixed to an end of the coil, the assistive anchoring force provided by the coil may be maximized, and not diminished by any twisting of the core during manipulation or positioning of the coil. Finally, such an arrangement may facilitate removal or repositioning of the device, since elongation of the coil when subjected to a longitudinal removing force may lessen the anchoring force supplied by the coil itself, making engagement with the introducing or removal apparatus easier.

The details of the construction or composition of the various elements of the vasoocclusion device 10 not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure.

INDUSTRIAL APPLICABILITY

The present invention is useful for establishing an embolus or occlusion in the vascular system, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A vasoocclusion device (10) for establishing an embolus or vascular occlusion in a vessel of a human or veterinary patient, the device (10) comprising:
   a floppy helical coil (12) having a proximal coil end (16), a distal coil end (18) spaced from the proximal coil end (16) and a coil lumen (20) defined therein extending between the proximal coil end (16) and the distal coil end (18);
   a core (22) disposed in at least part of the coil lumen (20), the core (22) having a proximal core end (24) and a distal core end (26); and
   one portion of the core (22) affixed to the helical coil (12) at a selected location, and the core extends from the selected location to a free end that remains unaffixed to the coil,
   wherein the core (22) provides the helical coil (12) with an anchoring force in the vessel (42), and the core (22) provides the helical coil (12) with a secondary nonlinear shape when unstressed in the vessel (42),
   wherein the secondary nonlinear shape of said helical coil (12) is predetermined by the core (22).

2. The device (10) as set forth in claim 1 wherein the coil lumen (20) possesses a defined cross-section, and the core (22) substantially fills the defined cross-section of the coil lumen (20).

3. The device (10) as set forth in claim 1 wherein the distal core end (26) is affixed to the distal coil end (18).

4. The device (10) as set forth in claim 3 wherein the distal core end (26) is soldered, welded or adhered to the distal coil end (18).

5. The device (10) as set forth in claim 1 adapted for introduction into the patient via a catheter (32), wherein the device (10) is detachably secured to the catheter (32).

6. The device (10) as set forth in claim 5 wherein the device (10) further comprises a reversible coupling (30) for detachably connecting the device (10) to the catheter (32) for introducing it into the patient.

7. The device (10) as set forth in claim 6 adapted for introduction into the patient via a pusher (34) contained in the catheter (32), wherein the coupling (30) detachably connects the device (10) to the pusher (34).

8. The device (10) as set forth in claim 1 wherein the core (22) comprises nitinol, another shape memory material, stainless steel or MP35N.

9. The device (10) as set forth in claim 1 wherein the core (22) comprises nitinol in a superelastic state.

10. The device (10) as set forth in claim 1 wherein the core (22) comprises nitinol in other than its stress induced, martensitic condition.

11. The device (10) as set forth in claim 1 wherein the secondary shape (60) is a saddle-type (62), helical type (64), vortex-type (66), irregular baffle-type (68) or fusiform helix-type (70) shape.

12. The device (10) as set forth in claim 1 wherein the secondary shape (60) is a substantially spherical secondary shape (72).

13. The device (10) as set forth in claim 12 wherein the substantially spherical secondary shape (72) is defined by circular loops (74) angularly spaced about an axis.

14. The device (10) as set forth in claim 12 wherein the substantially spherical secondary shape (72) is defined by D-shaped loops (78) angularly spaced about an axis.

15. The device (10) as set forth in claim 1 wherein the secondary shape (60) is an oval plate (84).

16. The device (10) as set forth in claim 15 wherein the oval plate secondary shape (84) is defined by a generally flattened array of loops of wire (14) and defining a plurality of holes through which other coils are deployable.

17. The device (10) as set forth in claim 1 further comprising a thrombogenic material (38) connected to or carried by the coil (12).

18. The device (10) as set forth in claim 17 wherein the thrombogenic material (38) comprises Dacron, cotton, silk, wool or polyester threads (44).

19. The device (10) as set forth in claim 1 wherein the helical coil (12) comprises a wire (14) having a wire diameter of about 0.010 in. to about 0.032 in. (about 0.25 m to about 0.81 mm).

20. The device (10) as set forth in claim 1 wherein the core (22) has a diameter of about 0.004 in. to about 0.015 in. (about 0.10 mm to about 0.38 mm).

21. The device (10) as set forth in claim 1 wherein the core is of nitinol and has a diameter of about 0.004 in. to about 0.006 in. (about 0.10 mm to about 0.15 mm), and the helical coil has a diameter of about 0.010 in. to about 0.015 in. (0.25 mm to 0.38 mm).

22. The device (10) as set forth in claim 1 wherein the core (22) includes at least one tapered end portion (46).

23. The device (10) as set forth in claim 22 wherein the core (22) includes two tapered end portions (46).

24. The device (10) as set forth in claim 1 wherein the core (22) defines alternating portions of larger (48) and smaller (50) diameters therealong having even and continuous transitions therebetween.

25. The device (10) as set forth in claim 1 wherein the secondary shape (36) of the coil (12) has a general outer dimension of about 3 mm to about 15 mm.

26. The device (10) as set forth in claim 1 wherein the helical coil (12) is about 2 to about 40 cm long when within a catheter.

27. A vasoocclusion device (10) for establishing an embolus or vascular occlusion in a human or veterinary patient, the device (10) being adapted for introduction into the patient via a catheter (32), and the catheter (32) having a pusher (34) contained therein for deploying the device (10) from the catheter (32); the device (10) comprising:

a floppy helical coil (12) having a proximal coil end (16), a distal coil end (18) spaced from the proximal coil end (16) and a coil lumen (20) defined therein extending between the proximal coil end (16) and the distal coil end (18);

a core (22) disposed in at least part of the coil lumen (20), the core (22) having a proximal core end (24) and a distal core end (26); and a thrombogenic material (38) connected to or carried by the helical coil (12);

wherein one and only one of the proximal core end (24) and the distal core end (26) is directly affixed to a respective one of the proximal coil end (16) and the distal coil end (18), the core extending therefrom to a core free end;

wherein the distal core end (26) is directly affixed to the distal coil end (18) by solder (28) or an adhesive;

wherein the core (22) comprises nitinol in a superelastic state, being in other than its stress induced, martensitic condition;

wherein the thrombogenic material (38) comprises Dacron, cotton, silk, wool or polyester threads (44); wherein the helical coil (12) comprises a wire (14) having a diameter of about 0.010 in. to about 0.032 in. (about 0.25 mm to about 0.81 mm);

wherein the core (22) has a diameter of about 0.004 in. to about 0.015 in. (about 0.10 mm to about 0.38 mm);

wherein the helical coil (12) is about 2 to about 40 cm long when constrained within a catheter; and wherein the core (22) provides the helical coil (12) with a secondary nonlinear shape, wherein the secondary nonlinear shape of said helical coil (12) is predetermined by the core (22), and an additional force assisting anchoring of the coil (12) in the human or veterinary patient when the helical coil (12) and the core (22) are deployed from the catheter (32).

28. A medical device (40) for establishing an embolus or vascular occlusion in a vessel of a human or veterinary patient, comprising:

a floppy helical coil (12) having a proximal coil end (16), a distal coil end (18) spaced from the proximal coil end (16) and a coil lumen (20) defined therein extending between the proximal coil end (16) and the distal coil end (18);

a core (22) disposed in at least part of the coil lumen (20), the core (22) having a proximal core end (24) and a distal core end (26);

one portion of the core (22) affixed to the helical coil (12) at a selected location, and the core extends from the selected location to a free end that remains unaffixed to the coil;

a catheter (32) dimensioned to receive the helical coil (12) and the core (22) therein; and a pusher (34) contained in the, catheter (32), adapted to deploy the coil (12) and the core (22) from the catheter (32);

wherein the core (22) provides the helical coil (12) with an anchoring force, and the core (22) provides the helical coil (12) with a secondary nonlinear shape in the vessel when the coil (12) and the core (22) are deployed from the catheter (32), wherein the secondary nonlinear shape of said helical coil (12) is predetermined by the core (22).

29. The device (10) as set forth in claim 28 further comprising a coupling (30) for detachably connecting the helical coil (12) to the pusher (34).

30. In a coil-type vasoocclusion device for establishing an embolus or vascular occlusion in a vessel of a human or veterinary patient, where the device comprises (a) a helical coil having a proximal coil end, a distal coil end spaced from the proximal coil end, a coil lumen defined therein extending between the proximal coil end and the distal coil end; and (b) a core disposed in at least part of the coil lumen, the core having a proximal core end and a distal core end; the improvement being characterized in that the helical coil is floppy and:

only one section of the core is affixed to the helical coil at a selected location such that the core has a free end, wherein the core provides the helical coil with a secondary nonlinear shape and an anchoring force in the vessel, wherein the secondary nonlinear shape of said helical coil is predetermined by the core.

31. The device as set forth in claim 30, wherein one of the proximal core end and distal core end is affixed to a respective one of the proximal helical coil end and the distal helical coil end.

* * * * *